United States Patent [19]

Shersher

[11] 3,974,527

[45] Aug. 17, 1976

[54] ARTIFICIAL HIP-JOINT FOR ARTHROPLASTY

[76] Inventor: Yakov Isaevich Shersher, 1 Degtyarny pereulok, 3, kv. 42, Saratov, U.S.S.R.

[22] Filed: Nov. 14, 1974

[21] Appl. No.: 523,794

[30] Foreign Application Priority Data

Nov. 19, 1973 U.S.S.R............................ 1967205

[52] U.S. Cl............................... 3/1.912; 128/92 C; 128/92 CA
[51] Int. Cl.² ........................................ A61F 1/24
[58] Field of Search ........................... 3/1.91–1.913, 3/1; 128/92 C, 92 CA

[56] References Cited
UNITED STATES PATENTS

| 3,102,536 | 9/1963 | Rose et al. | 128/92 CA |
| 3,656,184 | 4/1972 | Chambers | 3/1.91 |
| 3,795,922 | 3/1974 | Herbert et al. | 128/92 C X |
| 3,820,167 | 6/1974 | Sivash | 3/1.912 |

FOREIGN PATENTS OR APPLICATIONS 1,215,737  12/1970  United Kingdom............... 128/92 C Primary Examiner—Ronald L. Frinks
Attorney, Agent, or Firm—Haseltine, Lake & Waters

[57] ABSTRACT

An artificial hip-joint for arthroplasty comprising a first endoprosthesis of the acetabulum of a patient, coupled to a second endoprosthesis of the proximal portion of the femur rigidly connected by way of a neck with a pin insertable into the medullary canal of the femur. The first endoprosthesis is formed as a seat whereof the exterior surface is adapted to be impacted in the acetabulum, while the interior surface of the seat is spherical with a cavity of which the height being greater than the radius but smaller than its diameter. The head of the second endoprosthesis is of a spherical configuration and is provided with a centrally located opening; on the side thereof there is provided a cylindrical section disposed along the axis of the opening; eccentrically with respect to the center of the sphere.

2 Claims, 6 Drawing Figures

ARTIFICIAL HIP-JOINT FOR ARTHROPLASTY

The present invention relates to artificial joints for intra-articular prosthetic replacement and, more particularly, to artificial hip-joints for arthroplasty.

It is directed to assist in regaining hip-joint mobility lost in Bekhterev's disease, arthritis deformans, arthritis infectiosa, aceptic necrosis of the femoral head, as well as femoral neck fracture in the aged.

It is known in the art to employ an artificial hip-joint (USSR Inventor's Certificate No. 278,022 of Jan. 28, 1966) which comprises an endoprosthesis of the acetabulum hinged to an endoprosthesis of the proximal portion of the femur, with a spherical head rigidly fitted over a neck extending into an intraosseal pin.

The endoprosthesis of the acetabulum is formed as a seat whereof the exterior surface is formed as a plurality of tiered blades with sharpened edges, which blades are provided with apertures wherethrough burgeoning bony tissue may advance.

The interior surface of the seat of the acetabulum endoprosthesis has an irregularly shaped through opening composed of a cylindrical portion and a conical portion designed to receive two split inserts enveloping more than half of the sphere of the head of the endoprosthesis of the proximal portion of the femur. The endoprosthesis of the proximal portion of the femur is attached to the endoprosthesis of the acetabulum by riveting the split inserts onto the exterior surface of the endoprosthesis of the acetabulum.

The above-described known artificial hip-joint has some serious disadvantages stemming from the fact that it incorporates two inserts.

First of all, the processes of manufacturing the two inserts and machining the irregularly shaped recess formed in the acetabulum endoprosthesis seat are highly labor consuming.

Secondly, the riveting of the inserts causes the latter to be deformed.

Thirdly, the inserts cause the head of the endoprosthesis of the proximal portion of the femur to be reduced in size, thereby limiting the mobility of the joint.

Fourthly, with the endoprosthesis head reduced in size, the specific pressure per unit area of the sphere rises, adding to the wear of the joint surfaces.

It is an object of the present invention to eliminate the foregoing disadvantages.

A further object of the present invention is to provide an artificial hip-joint that is easy to manufacture.

Still another object of the present invention is to provide an artificial hip-joint affording a larger angle of joint movement.

Yet another object of the present invention is to provide an artificial hip-joint allowing the specific intraarticular pressure per unit area to be reduced.

These and other objects are attained by the inventive artificial hip-joint for arthroplasty which comprises an endoprosthesis of the acetabulum formed as a seat, whereof the exterior surface is formed as a plurality of tiered blades with sharpened edges, which blades are provided with apertures wherethrough burgeoning bony tissue may advance, and an endoprosthesis of the proximal portion of the femur, coupled with said seat. The latter endoprosthesis incorporates a spherical head with a centrally located opening to receive a neck whereby the head is linked with a pin introduced into the medullary canal of the femur. The interior surface of the first-mentioned endoprosthesis is made spherical, the height of the cavity of said sphere being greater than the radius but smaller than the diameter, and the head of the second-named endoprosthesis has a cylindrical section disposed on the side of the opening, which cylindrical section is disposed along the axis of the opening, eccentrically with respect to the centre of the sphere of the endoprosthesis head.

Besides, the opening in the head designed to receive the neck is disposed in the midportion of the cylindrical section.

Such a hip-joint structure is easy to manufacture, prevents sphere deformation, increases the angle of movement of the hinge joint, and reduces the specific intra-articular pressure per unit surface area. The proposed artificial hip-joint is sturdier, more reliable and has a longer service life than the prior art artificial hip-joints of the same type.

After a prosthetic replacement operation with the use of the proposed artificial hip-joint, the patients have a greater freedom of movement of the joint than in the case of the prior art artificial hip-joint built around two inserts.

The present invention will be further understood from the following detailed description of a preferred, exemplary embodiment thereof taken in conjunction with the accompanying drawings, wherein.

Figure 1:
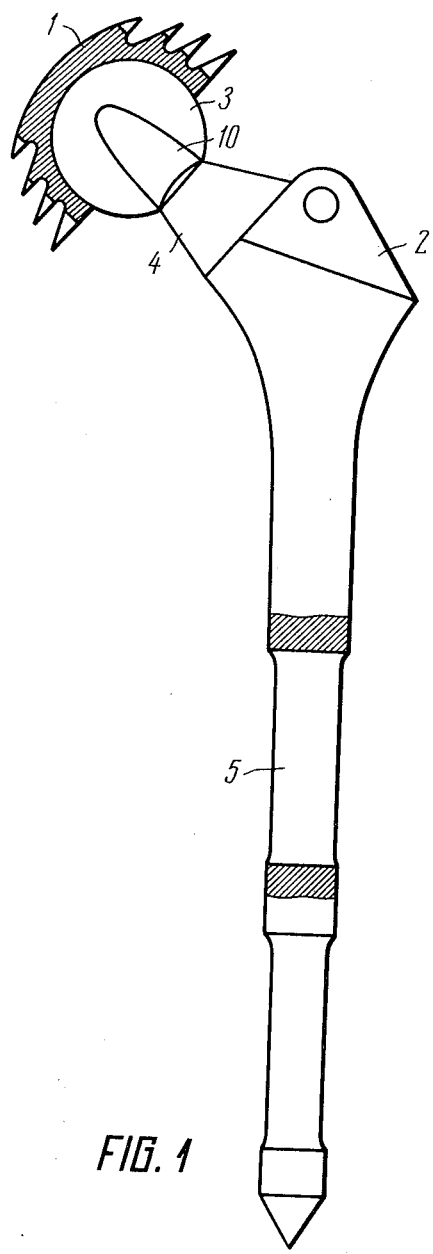
FIG. 1 is a general view, partially cut away, of an exemplary artificial hip-joint according to the invention.

Referring now to the drawings, the proposed artificial hip-joint for arthroplasty comprises an endoprosthesis 1 (FIG. 1) of the acetabulum and an endoprosthesis 2 of the proximal portion of the femur, the endoprostheses 1 and 2 being hinged one to the other. The endoprosthesis 2 of the proximal portion of the femur comprises a spherical head 3, a neck 4 and a pin 5 to be introduced into the femoral medullary canal.

Figure 2:
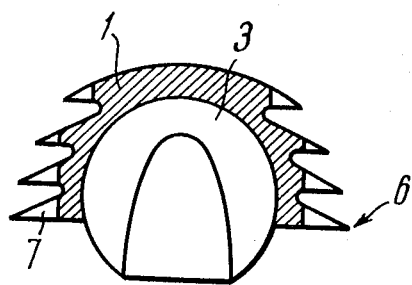
FIG. 2 illustrates hinging of the hip-joint as assembled.
Figure 3:
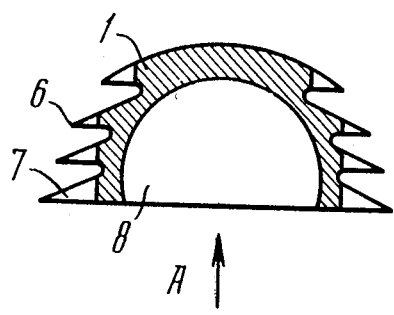
FIG. 3 is a longitudinal section of an endoprosthesis of the acetabulum shown in side elevation.
Figure 4:
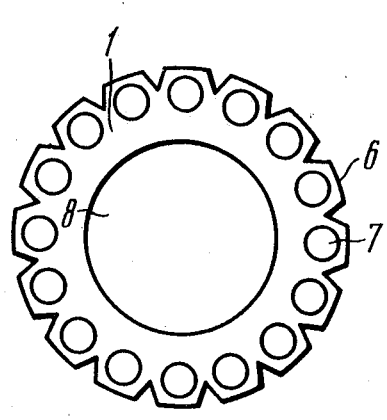
FIG. 4 is a view taken along the arrow A in FIG. 3.

The endoprosthesis 1 of the acetabulum (FIGS. 2, 3 and 4) is formed as a seat whereof the exterior surface is formed as a plurality of blades arranged in tiers. The edges of blades 6 are sharpened to ensure failsafe implantation into the acetabulum walls. The blades 6 are provided with apertures 7 wherethrough burgeoning bony tissue may advance.

Interior surface 8 (FIGS. 3 and 4) of the endoprosthesis 1 of the acetabulum is spherical, the height of the cavity of the sphere being greater than the radius but smaller than the diameter for holding the head 3 of the endoprosthesis 2 of the proximal portion of the femur.

Figure 5:
FIG. 5 is a side elevation of the head of an endoprosthesis of the proximal portion of the femur.
Figure 6:
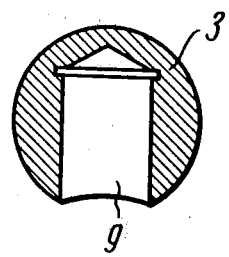
FIG. 6 is a longitudinal section of the head of an endoprosthesis of the proximal portion of the femur.

The head 3 (FIGS. 5 and 6) of the endoprosthesis 2 of the proximal portion of the femur is spherical in configuration and is provided with a centrally located opening 9 for receiving the neck 4. On the side of the opening 9 the head 3 has a cylindrical section 10 disposed along the axis of the opening 9, eccentrically with respect to the centre of the sphere of the head 3.

When putting the artificial hip-joint together, the head 3 is fitted into the endoprosthesis 1 of the acetabulum in such a way that the cylindrical section 10 registers with the entrance to the recess of the spherical interior surface 8. Then the head 3 is turned through 180°. When fitting the head 3 over the neck 4, the former has to be so positioned that the cylindrical section 10 is disposed on the sides with respect to the neck 4.

The foregoing hip-joint for arthroplasty ensures ease in manufacture, high reliability of the hinge joint, considerable mobility, and a long service life.

What is claimed is:

1. An artificial hip-joint for arthroplasty, such for the replacement of the affected acetabulum and the head of the femur of a patient, comprising a first endoprosthesis of the acetabulum, formed as a seat having an exterior surface and an interior surface; said exterior surface being defined by blades with sharpened edges and apertures through which growing bony tissue may protrude; said blades being arranged in circular rows that are in turn arranged in axially disposed tiers, one above the other; said interior surface of the seat having the shape of a sphere with a cavity that has a height greater than its radius but smaller than its diameter; a second endoprosthesis of the proximal portion of the femur, coupled with said seat and including a spherical head, a neck and a pin; said head has a radius corresponding to that of first endoprosthesis, for location of said head therein; the latter including a blind, substantially central opening for receiving said neck made in a body portion of said sphere; the exterior spherical surface of said head at the side of said opening having a cylindrical portion of a radius smaller than that of said sphere, to allow for the introduction of the head into said first endoprosthesis; said cylindrical portion being such that, at the introduction of said neck into said opening, it is positioned along the axis of said opening, eccentrically of said spherical head; said opening having an open end located at the side of said cylindrical portion; said pin being connected by one end through said neck with said spherical head, and being adapted to be introduced with its other end into the intraosseal canal of the femur.

2. The artificial hip joint as defined in claim 1, wherein said opening made in said body portion of the sphere is located in a midportion of said cylindrical portion.

* * * * *